(12) United States Patent
Badu-Tawiah et al.

(10) Patent No.: US 12,169,197 B2
(45) Date of Patent: Dec. 17, 2024

(54) THREAD SPRAY AMBIENT IONIZATION (71) Applicant: Ohio State Innovation Foundation, Columbus, OH (US)

(72) Inventors: Abraham Badu-Tawiah, Columbus, OH (US); Devin Swiner, Upper Marlboro, MD (US); Sierra Jackson, New Orleans, LA (US)

(73) Assignee: Ohio State Innovation Foundation, Columbus, OH (US)

( * ) Notice: Subject to any disclaimer, the term of this patent is extended or adjusted under 35 U.S.C. 154(b) by 573 days.

(21) Appl. No.: 17/600,834

(22) PCT Filed: Apr. 1, 2020

(86) PCT No.: PCT/US2020/026131
§ 371 (c)(1),
(2) Date: Oct. 1, 2021

(87) PCT Pub. No.: WO2020/205945
PCT Pub. Date: Oct. 8, 2020

(65) Prior Publication Data
US 2022/0187284 A1     Jun. 16, 2022

Related U.S. Application Data

(60) Provisional application No. 62/827,395, filed on Apr. 1, 2019.

(51) Int. Cl.
*G01N 33/53*     (2006.01)
*G01N 1/10*     (2006.01)
(Continued)

(52) U.S. Cl.
CPC ............... *G01N 33/53* (2013.01); *G01N 1/10* (2013.01); *G01N 1/4044* (2013.01);
(Continued)

(58) Field of Classification Search
CPC ...... G01N 33/53; G01N 33/6848; G01N 1/10; G01N 1/4044; H01J 49/022; H01J 49/0409; H01J 49/165
(Continued)

(56) References Cited

U.S. PATENT DOCUMENTS

| 3,224,497 A | 12/1965 | Blomgren et al. |
| 3,938,345 A | 2/1976 | Yamaga et al. |

(Continued)

OTHER PUBLICATIONS

International Searching Authority (ISA/US). International Search Report and Written Opinion, issued in PCT Application No. PCT/US2020/026131 on Jun. 9, 2020. 9 pages.
(Continued)

*Primary Examiner* — Kiet T Nguyen
(74) *Attorney, Agent, or Firm* — Meunier Carlin & Curfman LLC (57) ABSTRACT

Disclosed herein are methods and apparatus useful for the collection, preservation, and analysis of biological fluids. In some embodiments, a hydrophobic thread is contacted with a biological sample. The hydrophobic thread stabilizes the biological sample over prolonged periods of time. Compounds, including small molecules and/or biopolymers, can be ionized by applying a suitable voltage to the tread. These ionized compounds can then be analyzed, for instance using mass spectrometry.

18 Claims, 7 Drawing Sheets

(51) Int. Cl.
  G01N 1/40       (2006.01)
  G01N 33/68      (2006.01)
  H01J 49/02      (2006.01)
  H01J 49/04      (2006.01)
  H01J 49/16      (2006.01)
(52) U.S. Cl.
  CPC ........ G01N 33/6848 (2013.01); H01J 49/022 (2013.01); H01J 49/0409 (2013.01); H01J 49/165 (2013.01)
(58) Field of Classification Search
  USPC .......................................................... 250/288
  See application file for complete search history.

(56) References Cited

U.S. PATENT DOCUMENTS

| | | | |
|---|---|---|---|
| 2006/0022018 A1* | 2/2006 | Yoshimura | B23K 3/0361 228/55 |
| 2018/0330932 A1 | 11/2018 | Takats | |
| 2019/0006165 A1* | 1/2019 | Corr | H01J 49/165 |

OTHER PUBLICATIONS

Jackson, Sierra. Development of Thread Spray Mass Spectrometry for Direct Analysis of Capsaicinoids in Complex Pepper Products. Presented in Partial Fulfillment of the Requirements for the Degree Master of Science in the Graduate School of The Ohio State University, Graduate Program in Chemistry. 2017. Downloaded from https://etd.phiolink.edu/apexprod/rws_etd/send_file/send?accession=osu1499964339479481&disposition=inline. 60 pages.

Kim, Jiyun, et al. Fiber composite slices for multiplexed immunoassays. Biomicrofluidics 9.4: 044109. Jul. 29, 2015. 10 pages.

Swiner, Devin J., et al. Microsampling with cotton thread: Storage and ultra-sensitive analysis by thread spray mass Spectrometry. Analytica chimica acta 1082: 98-105. Jul. 9, 2019.

International Preliminary Report on Patentability issued for Application No. PCT/US2020/026131, dated Oct. 14, 2021.

Berggren, W. Travis, Michael S. Westphall, and Lloyd M. Smith. "Single-pulse nanoelectrospray ionization." Analytical chemistry 74.14 (2002): 3443-3448.

Bushey, Jared M., et al. "Pulsed nano-electrospray ionization: characterization of temporal response and implementation with a flared inlet capillary." Instrumentation Science and Technology 37.3 (2009): 257-273.

Chen, Fan, et al. "Applying mass spectrometry to study non-covalent biomolecule complexes." Mass spectrometry reviews 35.1 (2016): 48-70.

Chen, Fengming, et al. "Single-cell analysis using drop-on-demand inkjet printing and probe electrospray ionization mass spectrometry." Analytical chemistry 88.8 (2016): 4354-4360.

Damon, Deidre E., et al. "Direct biofluid analysis using hydrophobic paper spray mass spectrometry." Analytical chemistry 88.3 (2016): 1878-1884.

Deng, Jiewei, et al. "Surface-coated probe nanoelectrospray ionization mass spectrometry for analysis of target compounds in individual small organisms." Analytical chemistry 87.19 (2015): 9923-9930.

Ebeling, Daniel D., et al. "Corona discharge in charge reduction electrospray mass spectrometry." Analytical chemistry 72.21 (2000): 5158-5161.

El-Faramawy, Ayman, K. W. Siu, and Bruce A. Thomson. "Efficiency of nano-electrospray ionization." Journal of the American Society for Mass Spectrometry 16.10 (2005): 1702-1707.

Gong, Xiaoyun, et al. "Boosting the signal intensity of nanoelectrospray ionization by using a polarity-reversing high-voltage strategy." Analytical Chemistry 89.13 (2017): 7009-7016.

Huang, Guangming, et al. "Rapid screening of anabolic steroids in urine by reactive desorption electrospray ionization." Analytical chemistry 79.21 (2007): 8327-8332.

Huang, Guangming, Guangtao Li, and R. Graham Cooks. "Induced nanoelectrospray ionization for matrix-tolerant and high-throughput mass spectrometry." Angewandte Chemie International Edition 50.42 (2011): 9907-9910.

Kelly, Ryan T., et al. "Dilution-free analysis from picoliter droplets by nano-electrospray ionization mass spectrometry." Angewandte Chemie 121.37 (2009): 6964-6967.

Kulyk, Dmytro S., Colbert F. Miller, and Abraham K. Badu-Tawiah. "Reactive charged droplets for reduction of matrix effects in electrospray ionization mass spectrometry." Analytical chemistry 87.21 (2015): 10988-10994.

Li, Anyin, et al. "Triboelectric nanogenerators for sensitive nano-coulomb molecular mass spectrometry." Nature nanotechnology 12.5 (2017): 481-487.

Liang, Xiaorong, Yu Xia, and Scott A. McLuckey. "Alternately pulsed nanoelectrospray ionization/atmospheric pressure chemical ionization for ion/ion reactions in an electrodynamic ion trap." Analytical chemistry 78.9 (2006): 3208-3212.

McEwen, Charles N., Richard G. McKay, and Barbara S. Larsen. "Analysis of solids, liquids, and biological tissues using solids probe introduction at atmospheric pressure on commercial LC/MS instruments." Analytical Chemistry 77.23 (2005): 7826-7831.

Miller, Colbert F., et al. "Re-configurable, multi-mode contained-electrospray ionization for protein folding and unfolding on the millisecond time scale." Analyst 142.12 (2017): 2152-2160.

Qiao, Liang, et al. "Electrostatic-spray ionization mass spectrometry." Analytical chemistry 84.17 (2012): 7422-7430.

Rahman, Md Matiur, and Konstantin Chingin. "Stable and reproducible nano-electrospray ionization of aqueous solutions and untreated biological samples using ion current limitation combined with polarity reversing." Analytical Methods 11.2 (2019): 205-212.

Ren, Yue, et al. "Direct mass spectrometry analysis of biofluid samples using slug-flow microextraction nano-electrospray ionization." Angewandte Chemie International Edition 53.51 (2014): 14124-14127.

Sarver, Scott A., et al. "A comparison of alternating current and direct current electrospray ionization for mass spectrometry." Journal of The American Society for Mass Spectrometry 25.4 (2014): 524-529.

Sekimoto, Kanako, and Mitsuo Takayama. "Fundamental Processes of Corona Discharge." J. Inst. Electrostat. Jpn 33 (2009): 38-42.

Sekimoto, Kanako, and Mitsuo Takayama. "Negative ion formation and evolution in atmospheric pressure corona discharges between point-to-plane electrodes with arbitrary needle angle." The European Physical Journal D 60.3 (2010): 589-599.

Susa, Anna C., Zijie Xia, and Evan R. Williams. "Native mass spectrometry from common buffers with salts that mimic the extracellular environment." Angewandte Chemie International Edition 56.27 (2017): 7912-7915.

Susa, Anna C., Zijie Xia, and Evan R. Williams. "Small emitter tips for native mass spectrometry of proteins and protein complexes from nonvolatile buffers that mimic the intracellular environment." Analytical chemistry 89.5 (2017): 3116-3122.

Wei, Zhenwei, et al. "Rapid removal of matrices from small-volume samples by step-voltage nanoelectrospray." Angewandte Chemie International Edition 52.42 (2013): 11025-11028.

Zhang, Zezhen, et al. "Electro-kinetic assisted electrospray ionization for enhanced complex sample analysis." Talanta 164 (2017): 45-51.

Zhang, Zezhen, et al. "Electrophoretic desalting to improve performance in electrospray ionization mass spectrometry." Analytical chemistry 90.6 (2018): 3856-3862.

Zhao, Feifei, et al. "Joule heating and thermal denaturation of proteins in nano-ESI theta tips." Journal of The American Society for Mass Spectrometry 28.10 (2017): 2001-2010.

* cited by examiner

THREAD SPRAY AMBIENT IONIZATION

CROSS-REFERENCE TO RELATED APPLICATION

This application is a national stage application filed under 35 U.S.C. § 371 of PCT/US2020/026131 filed Apr. 1, 2020, which claims the benefit of U.S. Provisional Application 62/827,395, filed on Apr. 1, 2019, the contents of which are hereby incorporated in its entirety.

BACKGROUND

Microsampling is essential for the rapidly changing healthcare system where the sustainable implementation of biobanks (collection and storage of biological specimens) is expected to reduce operational cost and increase access to wider/different population groups. This exciting new paradigm is challenged by difficulties in manipulating small sample volumes and analyte homogeneity. For example, since there are currently no efficient methods for direct analysis of microsamples, dilution steps are necessary to convert the small sample volume into a form that can be handled by traditional large volume analytical methods. This dilution step not only increases analysis time, but it also negatively impacts the stability, storage and integrity of the sample. The accuracy of low-volume aliquots can be low, and the analysis of the diluted sample requires a more sensitive instrument, one that might not be readily available in resource-limited settings. The second key challenge is the uneven analyte distribution in the collected sample, for instance a significant issue in dried blood spots (DBS) prepared in paper substrates. Safeguarding homogeneity in small volumes of liquid samples (<20 µL) is also not trivial due to (i) sample loss via potential adsorption of analyte to the wall of the container and the fact that (ii) cold storage of small sample volumes often lead to unfavorable volume/surface ratios that results in evaporation (free-drying) after prolong storage.

Currently, the collection of small liquid samples is achieved via capillary microsampling (CM), which has significantly improved toxicology studies by reducing the number of animals required for safety assessment during drug development. After dilution, the collected blood sample is processed to plasma and stored under cold conditions for further downstream analysis in the laboratory. Remote sampling is more effectively achieved via collection platforms that allow dry-state sample storage. Lyophilization (freeze-drying) and vitrification (transformation into a "glass" state) have been used, but both techniques require resources and large volumes of blood. Volumetric absorption microsampling (VAM) has been proposed and recently found to offer superior analyte recovery, stability and homogeneity compared with the traditional DBS method. Like CM, however, direct sample analysis from VAM is not possible, requiring extensive sample preparations.

There remains a need for improved methods and systems for microsampling.

SUMMARY

Disclosed herein are methods and apparatus useful for the collection, preservation, and analysis of biological fluids. In some embodiments, a hydrophobic thread is contacted with a biological sample. The hydrophobic thread stabilizes the biological sample over prolonged periods of time. Compounds, including small molecules and/or biopolymers, can be ionized by applying a suitable voltage to the tread. These ionized compounds can then be analyzed, for instance using mass spectrometry.

BRIEF DESCRIPTION OF THE FIGURES

FIGS. 4A-4D depict (FIG. 4A) Schematic of agarose bead sampling methodology via 60-minute treated thread.

FIGS. 6A-6D depict the (FIG. 6A) extraction efficiency as a function of time for pure solutions of benzoylecgonine.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Figure 1:
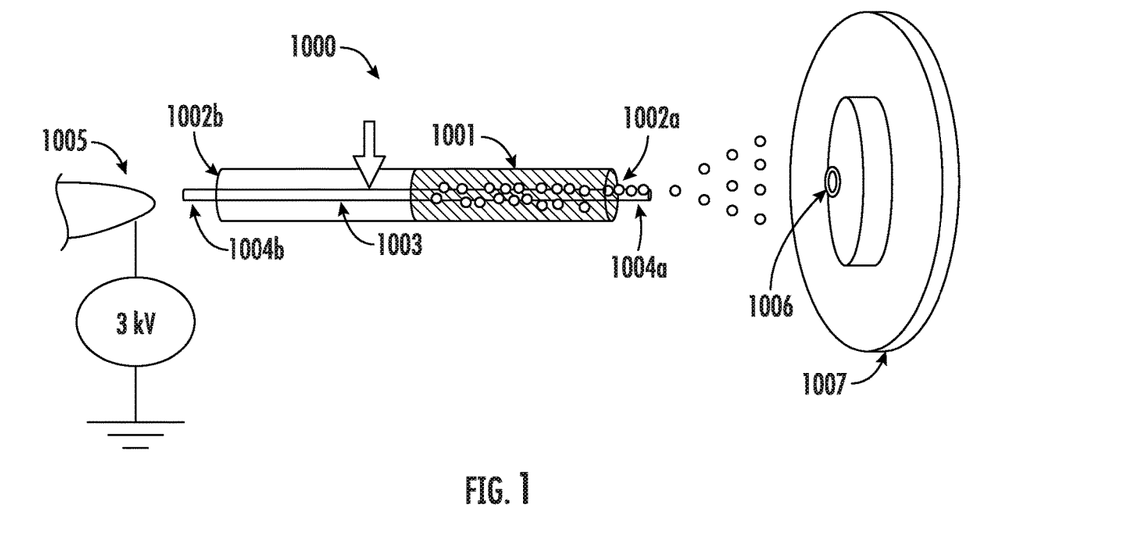
FIG. 1 illustrates a system for ionizing a compound according to one implementation.

Disclosed herein are systems, methods and apparatuses for ionizing organic compounds in an analyte sample, including small molecules and biopolymers. For example, FIG. 1 illustrates an exemplary system 1000 for ionizing organic compounds in an analyte sample. The system 1000 includes a non-conductive chamber 1001 having a first, distal opening 1002a, and a second, proximate opening 1002b, that are axially spaced apart. A thread 1003 having a first end 1004a and a second end 1004b can be contacted with an analyte containing at least one ionizable organic compound. The first end 1004a of the thread 1004 is urged into the chamber 1001 via the proximal opening 1002b and advanced towards the distal opening 1002a of the chamber 1001. As depicted in FIG. 1, the first end 1004a of the thread 1004 may be advanced axially beyond a plane that includes the distal opening 1002a of the non-conductive chamber 1001. In other embodiments, the first end 1004a of the thread 1004 may be coextensive with the plane that includes the distal opening 1002a of the non-conductive chamber 1001, or the first end 1004a of the thread 1004 may be disposed axially inwardly of the plane that includes the distal opening 1002a of the chamber 1001.

A voltage, for instance a direct current (DC) voltage, is directly applied to the thread 1004 via an electrode 1005 that contacts the thread. The voltage is sufficient to ionize the at least one ionizable organic compound.

At least a portion of the ionized organic compounds flow to an inlet port 1006 of an analyzer 1007. The analyzer is in fluid communication with the distal opening 1002a of the non-conductive chamber 1001. In certain embodiments, the analyzer is a mass spectrometer, for instance ion trap mass spectrometers, Orbitrap mass spectrometers, or triple quadrupole mass spectrometers.

In some embodiments, the analyte is a biological in origin. Exemplary biological analytes include extracellular fluid (i.e., fluid occurring outside of cells), intracellular fluid (i.e., fluid occurring within cells), transcellular fluid (fluids formed from transport activity in cells), and biological tissues. In some embodiments, the analyte can include urine, whole blood, blood serum, plasma, lymph, saliva, sweat, tears, cerebrospinal fluid, ocular fluid, joint fluid, gastrointestinal fluid, stomach acid, pancreatic fluid, serous fluid, synovial fluid, aqueous humor of the eye, perilymph, or endolymph.

Suitable threads for the systems, methods, and apparatuses disclosed herein include those having a cellulosic component. Exemplary cellulosic materials include cotton, kenaf, flax, hemp, jute, rayon, sisal, caroa, banana, coconut, wool, rye, wheat, rice, sugar cane, bamboo, or a combination thereof. In some instances, the thread can also include synthetic materials, for instance carbon fibers, polyethylenes, polyesters, polyamides, phenol-formaldehydes, polyvinyl chlorides, polyurethanes, or a combination thereof. When the thread is a mixture of cellulosic and synthetic materials, it is preferred that the cellulosic material constitutes at least 50%, at least 60%, at least 70%, at least 80%, or at least 90% of the total thread weight.

Threads suitable for the disclosed systems, methods, and apparatuses can have a size from about 5-100 wt., from about 5-80 wt., from about 10-70 wt., from about 20-60 wt., from about 30-50 wt., from about 10-50 wt., from about 10-30 wt., from about 20-40 wt., from about 10-20 wt., from about 40-60 wt., or from about 60-80 wt.

In certain embodiments, the cellulosic component may be functionalized. The hydroxyl functional groups present in cellulosic materials may be capped with hydrophilic or hydrophobic groups. Exemplary functional groups include silanes, which may be installed by reacting the thread with a compound having the formula:

wherein $R^1$, $R^2$, $R^3$, and $R^4$ are independently selected from OH, $R^a$, $OR^a$, $NHR^a$, $N(R^a)_2$, $OC(P)R^a$, F, Cl, Br, or I, wherein $R^a$ is in each case selected from $C_{1-12}$alkyl, aryl, heteroaryl, and heterocyclyl, and wherein any two or more of $R^1$, $R^2$, $R^3$, and $R^4$ can together form a ring. Suitable silanes may be installed by contacting the thread with a vapor that includes the silane compound.

Threads suitable for use in the disclosed invention may be characterized by their surface energy. For instance, in some embodiments, the thread can have a surface energy no greater than 30 mN/m, no greater than 32.5 mN/m, no greater than 35 mN/m, no greater than 37.5 mN/m, no greater than 40 mN/m, no greater than 42.5 mN/m, or no greater than 45 mN/m.

Threads suitable for use in the disclosed invention may be characterized by their surface roughness ($S_z$). For instance, in some embodiments, the thread can have a surface roughness ($S_z$) from 10-100 AU, from 10-80 AU, from 10-60 AU, from 10-40 AU, from 10-20 AU, from 20-60 AU, between 20-40 AU, from 30-60 AU, or from 30-50 AU.

In some embodiments, the thread can be functionalized with an antibody, for instance a monoclonal antibody. Such antibodies can be conjugated to the hydroxyl groups in the cellulosic component using conventional chemistries.

In some embodiments, the non-conductive chamber can be composed of glass, for instance a glass capillary. In some embodiments, the proximate opening and distal opening can be approximately the same size. For instance, the non-conductive chamber can have an inner diameter from 0.1-30 mm, from 0.5-20 mm, from 0.5-10 mm, from 0.5-5 mm, from 0.5-2.5 mm, from 0.5-1.5 mm, from 1-2 mm, from 2-3 mm or from 3-5 mm. In other embodiments, the proximate opening is larger than the distal opening.

In preferred embodiments, the outer diameter of the non-conductive chamber is slightly smaller than the inner diameter of the analyzer inlet port. In some embodiments, there is an air gap between the distal end of the non-conductive chamber and the inlet port, for instance from 0.5-10 mm, from 0.5-7.5 mm, from 2.5-7.5 mm, or from 4-6 mm. In further embodiments, the distal end of the non-conductive chamber directly contacts the inlet port, so that there is no air gap.

In some embodiments, the non-conductive chamber is cylindrical in shape, meaning that a cross-section taken perpendicular to the longest length of the non-conductive chamber will be substantially circular in shape. In other embodiments, other shapes may be present, for instance those defined by ovals or polygons (triangles, rectangles, squares, trapazoids, pentagons, hexagons, etc.).

A direct current voltage is applied to the thread in an amount sufficient to ionize at least one organic compound. For instance, the applied voltage can be at least about 0.5 kV, at least about 1.0 kV, at least about 1.5 kV, at least about 2.0 kV, at least about 2.5 kV, at least about 3.0 kV, at least about 3.5 kV, at least about 4.0 kV, at least about 4.5 kV, at least about 5.0 kV, at least about 6.0 kV, at least about 7.0 kV, at least about 8.0 kV, at least about 9.0 kV, or at least about 10.0 kV. In certain embodiments, the applied direct current voltage can be from 0.5-15 kV, from 0.5-10 kV, from 1-15 kV, from 1-10 kV, from 1-5 kV, from 2-10 kV, from 2-7 kV, or from 2-5 kV.

Figure 2:
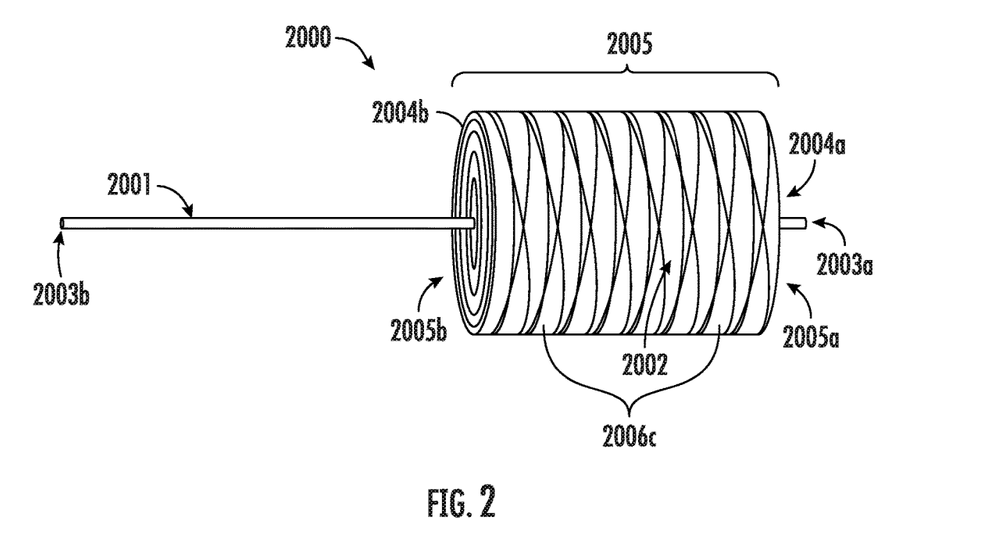
FIG. 2 illustrates a rod having a thread coiled around a portion thereof according to one implementation.

Also provided herein are coiled thread suitable as precursors for the ionization methods disclosed herein. In some implementations, a thread, as defined above, is coiled around a rod. The coiled thread facilitates sample application and adherence to the thread. The wetted thread can be delivered to the non-conductive chamber by unspooling the coiled thread through the non-conductive chamber. The rod can include a conductive material, enabling it to function as an electrode for delivering a voltage to the thread.

FIG. 2 illustrates a threaded rod 2000 according to one such implementation. The threaded rod 2000 includes a rod 2001 and a thread 2002. The rod 2001 has a first end 2003*a* and second end 2003*b* and a central axis A-A extending between the first end 2003*a* and the second end 2003*b*. The thread 2002 has a first end 2004*a* and a second end 2004*b*. The first end 2004*a* of the thread is coupled to or near the first end 2003*a* of the rod, and at least a portion 2004*c* of the thread is coiled around a coil portion 2005 of the rod 2001. The rod 2001 is axially slidable through the coiled portion 2004*c* of the thread. The coiled portion 2004*c* of the has a first end 2005*a* and a second end 2005*b* that are axially spaced apart. As depicted in FIG. 2, the first end 2001*a* of the rod may extend beyond a plane that includes the first end 2005*a* of the coiled portion of the thread 2002. In other embodiments the first end 2001*a* of the rod may be coextensive with the plane that includes the first end 2005*a* of the coiled portion 2004*c* of the thread, or the first end 2001*a* of the rod may be disposed axially inwardly of the plane that includes the first end 2005*a* of the coiled portion 2004*c* of the thread.

In some embodiments, the length of the thread can be approximately the same as the length of the rod, while in other embodiments, the length of the thread is greater than the length of the rod. In yet further embodiments, the length of the rod is greater than the length of the thread.

Because the first end of the thread is coupled to the first end of the rod, sliding the rod axially while holding coil portion in fixed position causes the thread to unspool. Sliding the rod into a non-conductive chamber as defined above disposes the thread in the chamber in position for the ionization processes described herein. As mentioned before, if the rod includes a conductive material, a voltage source may be electrically connected to the rod in order to provide a suitable voltage to the thread.

Figure 3:
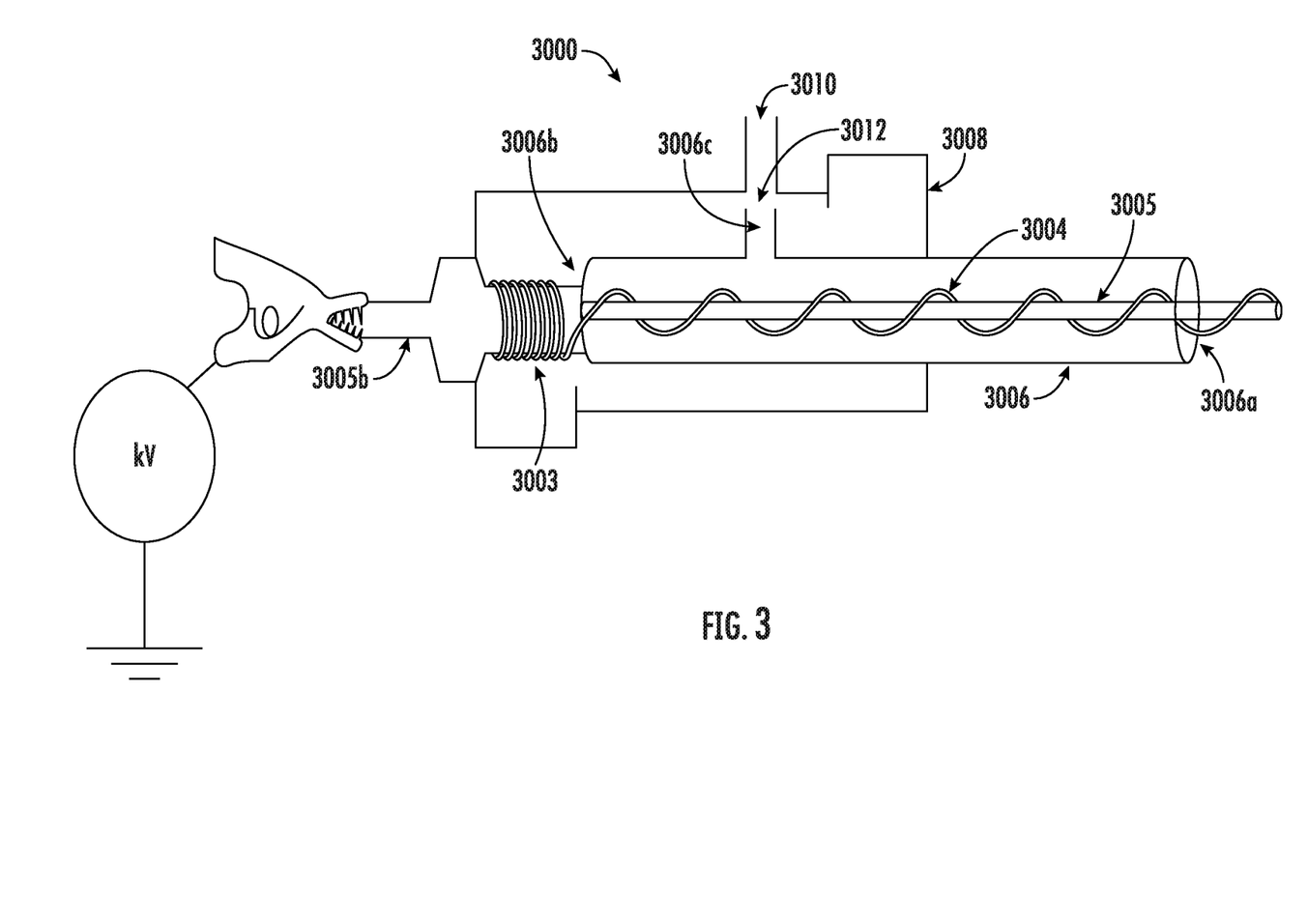
FIG. 3 illustrates a system for ionizing a compound using the rod with the coiled thread shown in FIG. 2, according to another implementation.

FIG. 3 depicts a system 3000 for ionizing a compound that includes the rod 3005, thread 3004, and non-conductive chamber 3006. The first end of thread 3004 can be attached to the first end of rod 3005*a*. The non-conductive chamber can be at least partially disposed within a housing 3008. The non-conductive chamber 3006 may be similar to the non-conductive chamber 1001 described above in relation to FIG. 1. A wall of the non-conductive chamber 3006 defines a solvent opening 3006*c* that is disposed between a distal opening 3006*a* and a proximal opening 3006*b* of the chamber 3006. Although the depicted implementation has a single solvent opening, in some embodiments, the non-conductive chamber can have a plurality of solvent openings. The housing 3008 defines a solvent inlet port 3010 that extends through a wall of the housing 3008. The solvent inlet port 3010 is in fluid communication with the solvent opening 3006*c* of the chamber 3006. Solvent introduced into the solvent inlet port 3010 and the solvent opening 3006*c* contacts the thread 3004 disposed within the chamber 3006. The housing 3008 can be used to position and stabilize the non-conductive chamber 3006 such that the distal opening 3006*a* of the chamber 3006 is adjacent the inlet port of the analyzer, such as the analyzers described above in relation to FIG. 1, and the second end of rod 3005*b* of the chamber 3006 is electrically connected with a voltage source, such as the voltage sources described above in relation to FIG. 1. In the embodiment depicted in FIG. 3, a portion of the thread is still in the coiled portion 3003, however, in other embodiments, the thread may be completely unspooled. In the implementation shown, the solvent port 3010 is fluidly coupled to the non-conductive solvent opening 3006*c*. In some implementations, the solvent port 3010 and the opening 3006*c* may be fluidly coupled via a tube that extends from the inlet port 3010 into the housing and is adjacent the opening 3006*c*. In other implementations, the solvent port 3010 and the solvent openings may be in direct contact or spaced apart from each other via an air gap.

In other implementations, the chamber 3006 may define more than one solvent opening 3006*c* between the proximal end 3006*a* and the distal end 3006*b* thereof. And, in other implementations, the chamber 3006 may not define any solvent openings 3006*c*, and the solvent can be applied to the thread through either the proximal end 3006*a* of the non-conductive chamber 3006 or the distal end 3006*b* of the non-conductive chamber 3006.

Because the trigger spray/ionization can be precisely controlled after a specified delayed extraction time, ultrasensitive analyte detection from untreated blood samples is achieved.

One aspect of the present invention provides improved collection, stabilization, and detection of protein biomarkers, without the need for cold storage. In that regard, an antibody-bound thread is used for sample collection; and labile protein biomarkers are selectively captured immediately upon sample application to the thread (or thread coil). Detection of the captured protein may be achieved (in one embodiment) through a sandwiched immunoassay with a reporter antibody that is also specific to the protein biomarker of interest. A reporter compound can be generated from the reporter antibody, and detected using mass spectrometry. Due to the high sensitivity of mass spectrometry for small molecules, sandwich complexes can be detected at low as picomolar concentrations. Unlike enzymes or gold nanoparticles, the immunoassay products (a "sandwich complex") are stable, permitting easy storage and transport of the thread device. Therefore, immunoassays performed as described are highly stable and able to be stored prior to analysis for extended periods of time.

The system includes a thread substrate conjugated to a capture antibody. The capture antibody binds the target antigen. The capture antibody may be conjugated to the thread substrate using conventional chemistries. In some embodiments, the capture antibody may simply be physically absorbed into the porous structure of the cellulose network. In other embodiments, a portion of the cellulose fibers may be modified to covalently conjugate with the capture antibody. In some embodiments, a portion of the cellulose fibers may be oxidized, e.g., to contain aldehyde groups, which then react with pendant amines in the capture antibody, resulting in a Schiff base, optionally using reductive conditions, resulting in a secondary amine.

In certain embodiments, the cellulose can be reacted with a compound having a first functional group that forms a covalent bond with the primary hydroxyl groups in the cellulose (or an oxidized derivative thereof, e.g., aldehyde or carboxylic acid), and a second functional group that can covalently bind to the capture antibody, or the second functional group can be converted to a moiety that can bind to the capture antibody. Exemplary first functional groups include epoxides and primary amines, exemplary second functional groups include primary alcohols. As used herein, a thread substrate modified in this manner is said to have a spacer between the cellulose and capture antibody. In other embodiments, the thread substrate can be conjugated to avidin using the techniques described above, and combined with a biotin labeled capture antibody.

Subsequent to installation of the capture antibody, the system can be reacted with a blocking group, for instance tris(hydroxymethyl)aminomethane ("Tris") in order to prevent non specific binding to the cellulose substrate.

The capture antibody-functionalized thread is then contacted with a biological sample suspected of containing the antigen. The thread is then contacted with a reporter antibody, resulting in a sandwich complex if antigen was present in the biological sample. After the sandwich complex has been formed, the thread is washed to remove any unbound reporter antibody, and subsequently treated to generate a reporter compound. The presence of the reporter compound can be determined using mass spectrometry. In that regard, a capture-antibody-bound thread is used for sample collection; and antigens are selectively captured immediately when a biological fluid is contacted with the thread. Unlike enzymes or gold nanoparticles, the sandwich complexes are stable, permitting easy storage and transport of the paper device. While metal tags have been used to enable amplification of MS signals, their release and ionization requires plasma sources, which in turn requires pressurized gases such as helium. As such, in preferred embodiments of the invention, the reporter antibodies do not include exogenous metal tags.

In some instances, the thread substrate can be conjugated to a plurality of capture antibodies, permitting the detection of a plurality of target analytes. Provided that different reporter compounds are associated with different reporter antibodies, a plurality of different antigens can be identified in a single assay.

Exemplary antigens that may be detected include cancer antigens (including tumor antigens), viral antigens, bacterial antigens, fungal antigens, parasitic antigens, neuronal antigens, and others. In certain preferred embodiments, the antigen is a marker for HIV, malaria, dengue, Chagas' disease, Leishmania, Trypanosoma, Plasmodium, Toxoplasma, adenovirus, *Campylobacter*, rotovirus, norovirus, *E. coli*, *Salmonella*, influenza, anthrax, *Legionella*, chlamydia, trachomatis, herpes simplex, gonorrhoeae, hepatitis (including A, B, C and other strains), measles, penuomonia, or tuberculosis.

The reporter antibody is functionalized to generate a small molecule reporter compound subsequent to sandwich complex formation. In some cases, the reporter antibody includes a quaternary ammonium group:

wherein AB is an antibody, SCL is a selectively cleavable linker, n is a number from 0-30 (e.g., 1-5, 2-7, 5-10, 5-15, 10-20, or 10-30), and each of $R^1$, $R^2$, and $R^3$ are independently selected from $C_{1-12}$alkyl, aryl, heteroaryl, and heterocyclyl, and wherein any two or more of $R^1$, $R^2$, and $R^3$ can together form a ring. In a preferred embodiment, each of $R^1$, $R^2$, and $R^3$ are methyl. For embodiments in which a plurality of capture antibodies are present, to form sandwich complexes with a plurality of reporter antibodies, it is preferred that the selectively cleavable linker is the same, but each reporter antibody includes a distinct constellation of $R^1$, $R^2$, and $R^3$ groups, so that each reporter compound can be detected in the same mass spectrometer analysis.

Cleavage of the linker generates a free quaternary ammonium compound, which can be detected at very low concentration using mass spectrometry. The selectively cleavable linker may be cleaved in response to a pH change, irradiation, oxidant, or reductant. Exemplary pH sensitive linkers include esters (for cleavage by hydrolysis), exemplary oxidant cleaved linkers include diazos, exemplary reductant cleaved linkers include disulfides, and exemplary irradiation cleaved linkers include ortho-nitrobenzyl ethers. In some instances, the reporter antibody can include:

wherein AB, n, $R^1$, $R^2$, and $R^3$ are as defined above;
$X^1$ is null, NH, O, or S, and $X^2$ is S or O;
m is a number from 0-20, 0-10, 0-5, 0-2, 2-20, 2-10, 2-5, 5-20, 5-10, or 10-20;
n is a number from 0-20, 0-10, 0-5, 0-2, 2-20, 2-10, 2-5, 5-20, 5-10, or 10-20;
p is a number from 0-20, 0-10, 0-5, 0-2, 2-20, 2-10, 2-5, 5-20, 5-10, or 10-20;
is in each case independently selected from 0, 1, 2, 3, or 4;

wherein one of $R^4$, $R^5$, $R^6$, $R^7$, $R^8$ (if present) is selected from:

and the remaining groups are independently selected from OH, $R^a$, $OR^a$, $NHR^a$, $N(R^a)_2$, $C(O)R^a$, $OC(O)OR^a$, $OC(O)R^a$, $NO_2$, cyano, F, Cl, Br, or I, wherein $R^a$ is in each case independently selected from $C_{1-12}$alkyl, aryl, heteroaryl, and heterocyclyl; and wherein $R^9$ is in each case independently selected from OH, $R^a$, $OR^a$, $NHR^a$, $N(R^a)_2$, $C(O)R^a$, $OC(O)OR^a$, $OC(O)R^a$, $NO_2$, cyano, F, Cl, Br, or I, wherein $R^a$ is in each case independently selected from $C_{1-12}$alkyl, aryl, heteroaryl, and heterocyclyl. In certain preferred embodiments, $R^5$, is alkoxy, e.g., methoxy, and $R^4$ and $R^7$ are each hydrogen.

In some embodiments, the selectively cleavable linker precursor compound includes an aldehyde:

wherein n, p, $R^1$, $R^2$, and $R^3$ are as defined above; $R^{10}$, $R^{11}$ and $R^{12}$ are independently selected from OH, $R^a$, $OR^a$, $NHR^a$, $N(R^a)_2$, $C(O)R^a$, $OC(O)OR^a$, $OC(O)R^a$, $NO_2$, cyano, F, Cl, Br, or I, wherein $R^a$ is in each case independently selected from $C_{1-12}$alkyl, aryl, heteroaryl, and heterocyclyl. In certain preferred embodiments, $R^{11}$, is alkoxy, e.g., methoxy, and $R^{10}$ and $R^{12}$ are each hydrogen. The precursor compound can be reacted with pendant amines in the reporter antibody as described above In other embodiments, the reporter antibody includes a photoredox catalyst component. The presence of the sandwich complex in the system can be determined by introducing a compound known to react when irradiated in the presence of the photocatalyst. In some cases the irradiated can be exposure to visible light, while in other cases a dedicated light source, e.g., a laser or flashlight can be employed. Exemplary photoredox catalysts include Rose Bengal, Eosin Y, TPP$^+$, Mes-Acr$^+$, and riboflavin type systems. A suitably functionalized photoredox catalyst may be conjugated to an antibody using conventional chemistries. In one embodiment, after formation of the sandwich complex and removal of the unreacted reported antibody, triethanolamine is introduced to the thread, which is converted to diethanolamine by the photoredox catalyst. Subsequent MS analysis can be used to detect the presence of diethanolamine, thus indicating the presence of the sandwich complex. In some analytical settings, the presence of esterases in certain blood sample can cause cleavage of the ester bond during assay. In such cases, the photoredox process or other pH-active functional groups (e.g., hydrazones, oximes, etc.) can be used as part of the structure of the probe to reduce esterase and other biological effects.

The following four steps can be used to prepare devices for the disclosed assay: (1) thread oxidation—oxidization of hydroxyl groups in cellulose to aldehyde groups—suitable methods include soaking the paper in 0.031 M $KIO_4$ solution and heating to 65° C. for 2 hours; (2) Covalent Antibody Binding on Paper; and (3) Blocking—empty sites in the paper test zones are blocked with Tris to prevent analyte non-specific binding.

By immobilizing a specific antibody that recognizes a particular disease biomarker, the resultant thread becomes a bioactive sensing device that can be used for the immunoassay.

Antigen capture: For the immunoassay step, a solution (e.g., blood, saliva) containing a target antigen (for instance PfHRP-2 and/or P. aldolase as malaria biomarkers) are added to the thread surface containing the immobilized antibody that recognizes a specific epitope on the biomarker. After incubation, the test zones are washed, for instance one or more times with PBS buffer.

The reporter antibody is then added to the thread. The binding of the reporter antibody to the antigen immobilizes the reporter antibody to the thread. A buffer wash step will remove unbound antibody.

Following the capture of analyte and reporter antibody, the sandwich complex can be treated to release the reporter compound. For hydrolytically labile linkers, a drop (5 μL) of an aqueous $NH_4OH$ basic solution will be applied to the thread to release the reporter compound, which will be detected using thread spray MS. Apart from the washing step, no purifications or amplifications are needed prior to analysis.

While in some embodiments a biological fluid may be directly applied to the thread or coiled thread, other methods of sample collection are also possible. For instance, a thread may be affixed to a needle, and then introduced into biological tissue. The threaded may be drawn through the biological tissue, or may be permitted to reside in contact with the tissue for prolonged periods of time, in order to facilitate absorption onto the thread.

EXAMPLES

The following examples are for the purpose of illustration of the invention only and are not intended to limit the scope of the present invention in any manner whatsoever.

In this work, we present an integrated thread-based microsampling platform capable of (i) direct analysis of the collected biological samples without dilution or pre-treatment, (ii) homogeneous distribution of analyte within the collected microsample, and (iii) dry-state room temperature storage of blood samples, without change in analyte integrity after prolong storage. Spooled cotton threads (30 or 50 wt.) were used as is (hydrophilic) or after treatment with the vapor of trichloro(3,3,3-trifluoropropyl) silane reagent. Sample collection was achieved simply by dipping the thread substrate directly into the blood. The vertical capillary action in thread substrates allowed for correct volume estimation for blood samples less than 10 µL. Unlike paper substrates that are anisotropic in nature, the individual fibers in thread are unidirectional providing highly controlled fluid flow. Dried blood samples present on the thread substrates were directly analyzed by thread spray mass spectrometry (MS). Here, the thread containing the sample is placed in a glass capillary and a suitable organic solvent (e.g., ethyl acetate, 20 µL) applied, which selectively extracts organic analytes from the blood sample. By fitting the threaded glass in front of a mass spectrometer and applying a direct current (DC) voltage to the wet thread, the extracted molecules present in the organic solvent are ionized and transferred to the mass spectrometer via an electrospray ionization mechanism. Since the thread is enclosed in the small capillary, solvent evaporation is effectively controlled, allowing up to 84% of organic compounds such as benzoylecgonine (log P −0.59) to be extracted from the thread substrate within 60 s using ethyl acetate. This is contrary to traditional substrate-based ambient ionization methods where the simultaneous application of both the spray solvent and voltage limits analyte extraction.

As a proof-of-concept, we chose to evaluate the sensitivity and stability of diazepam, which is important both in medicine and forensics. First, we sampled 10 µL of blood spiked with diazepam using untreated hydrophilic cotton thread.

Direct thread spray MS analysis of the untreated blood samples using 60 s extraction time resulted in excellent linearity in 0.2-100 ng/mL concentration range. This calibration function was constructed using isotopically labeled internal standard (IS), and monitoring analyte-to-internal standard ratio (A/SI) in tandem MS mode. Limit of quantification was determined to be 185 part per trillion (185 pg/mL). The 10 µL blood volume traveled an average distance of 16±1.7 mm along the thread substrate. To determine whether diazepam is homogeneously distributed along the entire 16 mm length, the thread substrate containing the blood sample was cut into two equal sections. Diazepam ion signal from each section was quantified. Comparable ion yield was recorded from both sections indicating uniform analyte distribution in the thread substrate, which we attribute to the uniform fluid flow in the unidirectional thread fibers. Further analysis showed that 10× improvement in ion yield was achieved when sample volume was increased by 4×. This result motivated us to alter the surface properties of the thread substrate in an attempt to increase analyte availability without increasing sample volume. We adopted hydrophobic silane treatment that is known to reduce absorption of aqueous-based samples. By using a bracketing method, we characterized the surface energies of the resultant treated hydrophobic threads as <34.4 and <33.0 mN/m for 30- and 60-min silane treatment times, respectively. As expected, limit of quantification (LOQ) for diazepam decreased by 5× when the treated hydrophobic threads were used in thread spray MS where the 30 and 60 min treated threads registered 80 and 34 part per trillion LOQs, respectively. This increase in sensitivity is attributed to increased extraction efficiency from the hydrophobic thread. Online in-capillary dissolution experiments have shown that >60% of analyte (log P 2.82) can be desorbed from a 60-min treated thread within 60 s extraction time compared with 40% for untreated hydrophilic thread. Interestingly, the in-capillary extraction process is found to be more efficient than the corresponding bulk-phase extraction performed using the same solvent volume. It should also be noted that the used thread can be stored and reanalyzed proving a unique opportunity to validate results and eliminate the need to increase sample volume via dilution.

For the purposes of comparing with other direct ionization methods (e.g., paper spray), and the fact diazepam is often abused with other illicit drugs, the limit of detection (LOQ) and LOQ for cocaine, amphetamine and methamphetamine were also determined using the thread spray MS methodology. In all cases, treated hydrophobic threads offered lower LODs and LOQs than direct analysis from untreated thread.

Relative standard deviations less than 10% were obtained at all concentrated tested for both treated and untreated threads, and excellent linearity ($R2>0.999$) and reproducibility were also recorded for all analytes. LOD as low as 13 pg/mL was calculated for amphetamine compared to 60 ng/mL previously determined using hydrophobic paper spray MS. This increase in sensitivity is associated with the delayed extraction capabilities in thread spray allowing more analytes to be extracted and detected. While the coupling of a separate solid-phase extraction (SPE) process with ambient ionization has resulted in improved sensitivity this combination cannot be used for microsamples since large volumes of biofluid (e.g., 0.01-1.5 mL) are required for the SPE step. It is important to point out that the SPE-based approaches have not been applied to analyze raw blood; it often utilizes less complex biofluids such as urine and plasmas. Realizing that the 60 s delayed extraction in thread spray is a form of SPE where the ethyl acetate spray solvent selectively transfers the extracted organic compound to the mass spectrometer leaving the bulk of the blood matrix immobilized on the thread substrate, we sought to characterize analytical performance of the thread spray MS methodology in low part per trillion concentration range. 2-100 pg/mL standard solutions of diazepam were spiked separately in 10 µL of untreated whole blood. This analysis was performed using 60-min treated hydrophobic thread substrates, which provided an unprecedented 25 part per quadrillion detection limit for diazepam (LOQ is 52 fg/mL) without sacrificing linearity, precision and reproducibility. This establishes thread spray as an ultra-sensitive ambient ionization technique enabling direct analysis of microsamples by mass spectrometry. The in-capillary sample processing is highly efficient in eliminating matrix effects and yielding results that are comparable to the most sensitive SPE surfaces but without the use of extra washing step, large sample volumes or specialized accessories like cartridges.

TABLE 1

Limits of detection and quantification, LOD (LOQ) in pg/mL, of illicit and pharmaceutical drugs in blood samples.

|  | Diazepam | Amphetamine | Methamphetamine | Cocaine |
| --- | --- | --- | --- | --- |
| Untreated | 131 (185) | 37 (65) | 43 (107) | 99 (142) |
| 30 minutes | 43 (80) | 28 (44) | 31 (50) | 44 (67) |
| 60 minutes | 17 (34) | 13 (18) | 16 (22) | 14 (22) |

Figure 5A:
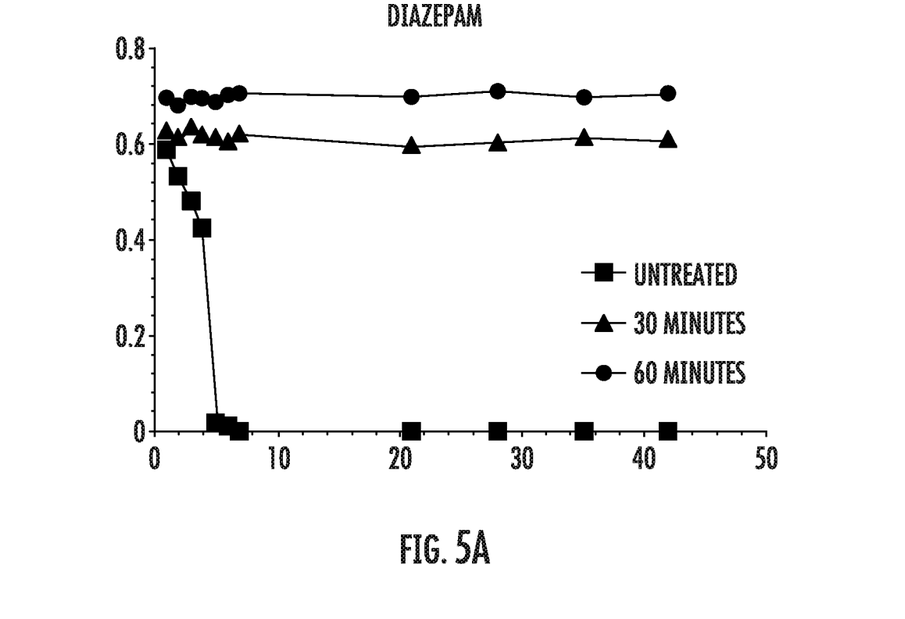
FIGS. 5A-5B depict the stability of (FIG. 5A) diazepam and (FIG. 5B) cocaine in whole blood on untreated, 30-minute treated, and 60-minute treated thread.
Figure 5B:
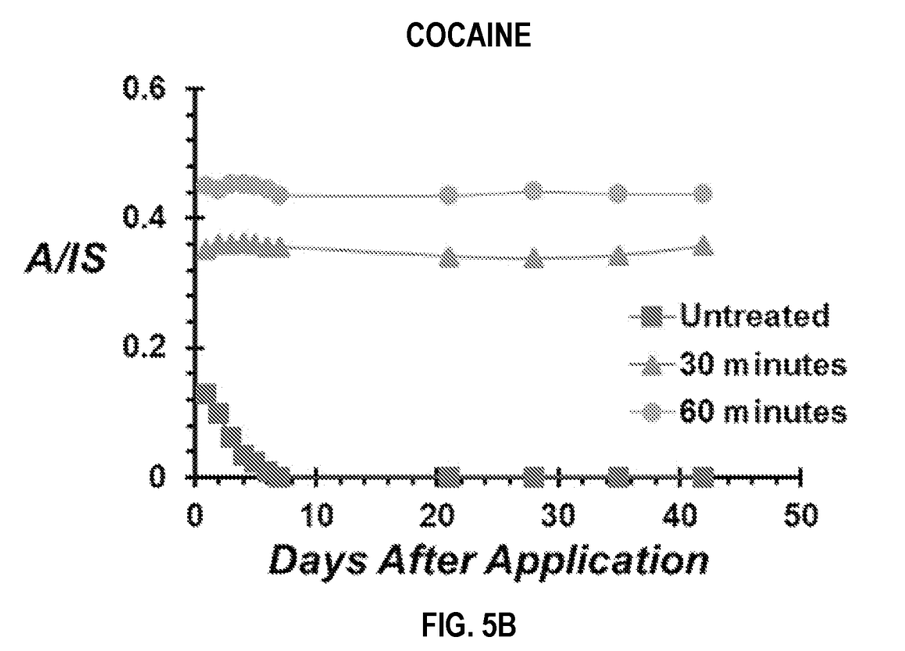
Figure 6A:
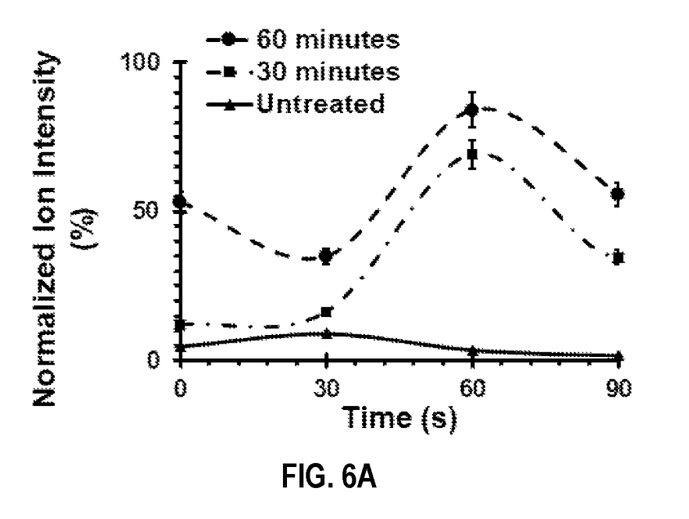
Figure 6B:
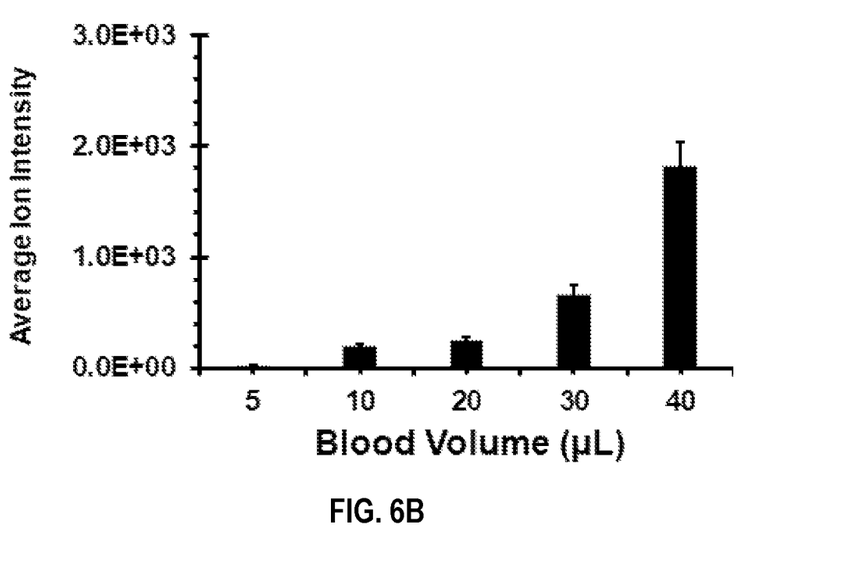
(FIG. 6B) average ion intensity as a function of blood volume for cocaine on 60-minute treated thread.
Figure 6C:
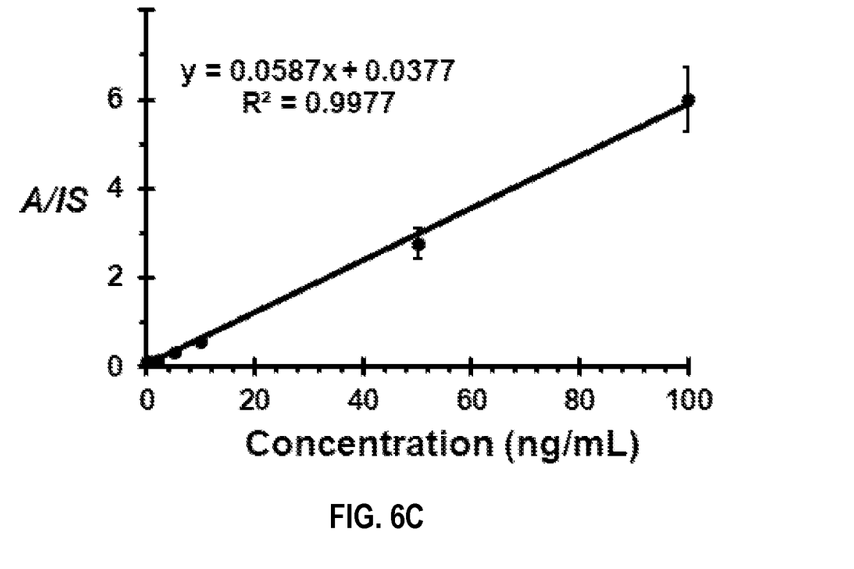
(FIG. 6C) calibration curve for diazepam in whole blood on untreated cotton thread.
Figure 6D:
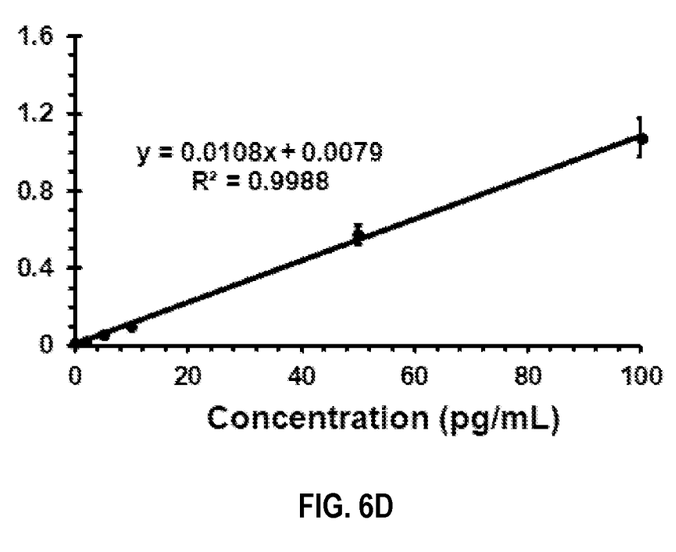
(FIG. 6D) ppt range calibration for diazepam in whole blood.

Storage is the main determining factor governing the stability of diazepam in blood. While varied diazepam stability have been reported under freezer (−20° C.) storage conditions, most studies agree on severe degradation when stored at room temperature. Therefore, we investigated the diazepam stability in blood after storage in treated and untreated thread substrates. The rapid flow of aqueous samples in untreated thread (radius 175 µm) resulted in the distribution of the 10 µL blood over a surface area of 17 mm² compared with 0.4 mm² for threated hydrophobic threads. This increased surface area-to-volume ratio predisposes the majority of the labile diazepam analyte present in the untreated thread substrate to oxidation. Diazepam degraded in less than 5 days after blood storage at room temperature in the untreated hydrophilic thread (FIG. 5A). On the contrary, the concentration of the 10 µL blood to a small area when stored on hydrophobic threads provided improved analyte stability (FIG. 5A). In this case, near-surface molecules provide transient passivation leading to limited thermal and/or oxidant flux into the sample and thus mitigating oxidation of analyte within the core of the stored blood over the entire six weeks period. Similar stability profiles were observed for cocaine in whole blood storage in untreated hydrophilic versus treated hydrophobic thread substrates (FIG. 5B). In all cases, the relative ion signal (A/IS) derived from the 60 min treated threads was higher than signal from the 30 min treated thread substrates. This is likely due to the higher efficiency of ionization from the more hydrophobic thread substrate. However, the marked reduction (~57%) in cocaine signal after the first day of storage on hydrophilic thread is consistent with rapid degradation in storage environment without protective surface layer as those observed in dried blood spot samples. The ability to detect diazepam and cocaine in biofluid samples over an extended period without sacrificing sensitivity or the integrity of the sample has important implications in forensics and clinical applications. In addition, the thread-based sampling and storage methodology uses small sample volumes and does not require special storage conditions making it ideal for field studies.

Figure 4A:
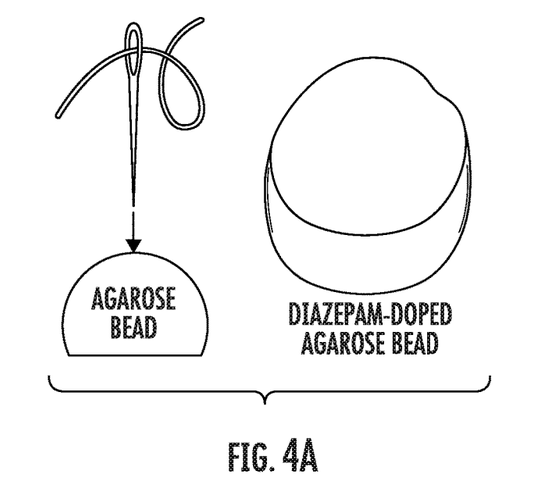

Diazepam is also commonly analyzed in postmortem biochemical investigation due to its role in accidental overdose. The concentration of diazepam changes rapidly after death due to decomposition and redistribution phenomenon so sensitive analytical methods for tissue samples can serve to complement biofluid analysis. To demonstrate this concept, we used soft tissue-mimicking agarose beads (5 mm, ID), which exhibit high water uptake and controllable permeation for oxygen and nutrients. The agarose beads were stored in a 96-well plate at 37° C. in 200 µL of McCoy's 5A media with 10% FBS and L-glutamine, which we removed to introduce diazepam into the agarose beads. For this, excess media was doped with varying concentrations of diazepam (50, 100, and 250 ng/mL) before adding 200 µL to each well. This drug-doped media was infused into the soft, porous agarose beads overnight before taking a threaded needle to punch through each sample (FIG. 4A). Agarose beads residues collected on the 60-min thread were analyzed directly by thread spray MS. Pink colored samples were deemed viable for analysis because they reflected the pink color of the media, suggesting that diffusion was successful, and were the only samples used for analysis.

Figure 4B:
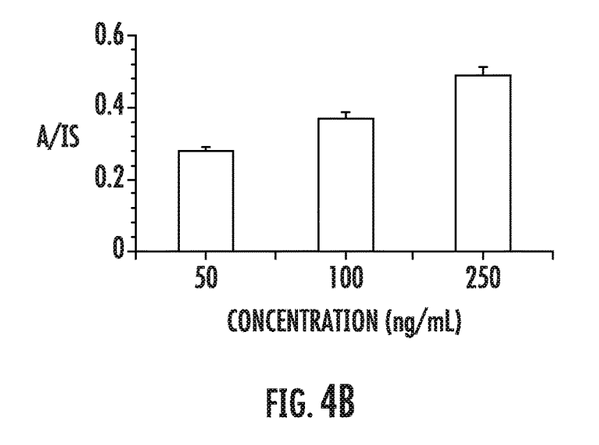
(FIG. 4B) concentration dependence of diazepam in agarose beads.
Figure 4C:
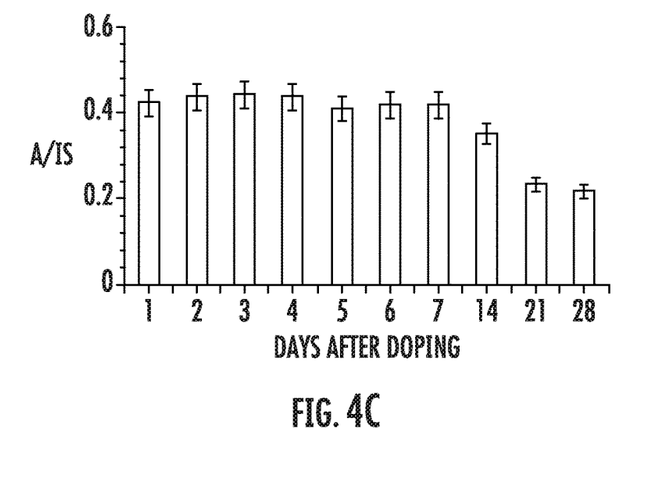
(FIG. 4C) decrease in concentration over 28 days of diazepam in agarose beads (FIG. 4D) diazepam fragmentation pattern in tandem MS studies.
Figure 4D:
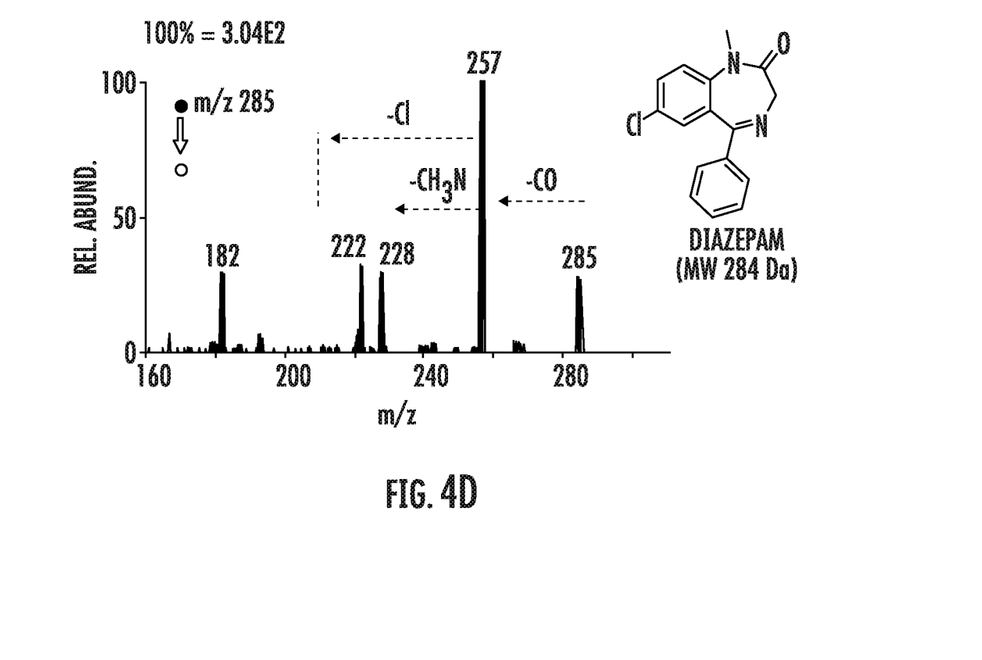

Similar to what we have seen with blood, there is an increase in signal intensity as the concentration increases (FIG. 4B), suggesting this method is capable of detecting varying analyte concentrations with statistical significance. Note that, unlike blood analysis where the whole sample is subjected to extraction, here only a small fraction of the agarose bead is collected, and yet intense ions are detected for diazepam via tandem MS (FIG. 4D). In this case, collision-induced dissociation was employed producing a diagnostic fragment ion at m/z 257 via CO (MW 28) neutral loss, which further dissociated to give ions at 228 and 222 through the elimination of nitrine ($CH_3N$; MW 29) and chlorine (Cl; MW 35) species. To further investigate sensitivity for this application, a stability test, in dry conditions, was performed. Fresh agarose beads were doped with diazepam (250 ng/mL) as described above and left overnight for analyte infusion. After the initial 24-hour period, diazepam-doped media was removed, and the dry agarose beads were stored at 37° C. for four weeks. Removal of the media was done to mimic tissues storage under post-mortem conditions, where proper nutrients are not available to keep them alive. Analysis for this study included daily sampling in the first week followed by weekly analysis for three more weeks. Diazepam signal was stable in the first week of storage suggesting the agarose samples stayed viable. There was a visible change from pink to brown color after the second week, which may indicate onset of oxidation of the agarose beads. This fact was reflected in the thread spray MS signal where a noticeable drop in ion yield was continuously detected after the second week. (FIG. 4C). This gradual degradation of the agarose samples, and in turn the analyte, was expected due to the porous nature of the agarose beads and, with the steady detection and identification of diazepam in these samples, further validates thread spray as a sensitive technique that could be used for post-mortem analyses.

In conclusion, we have proven that the use of thread, both hydrophilic and hydrophobic are both viable substrates for biological fluid analyses. The advantages of surface modifications, uniform diffusion, and online extractions directly influence the sensitivity of this method for use in various applications. Thread can be used as an all-in-one substrate for sample collection, storage, and direct analysis over extended periods of time and its parts-per-quadrillion detection limit make it an attractive alternative to other substrate-based ambient methods.

The devices, kits, and methods of the appended claims are not limited in scope by the specific compositions and methods described herein, which are intended as illustrations of a few aspects of the claims and any devices, kits, and methods that are functionally equivalent are intended to fall within the scope of the claims. Various modifications of the devices, kits, and methods in addition to those shown and described herein are intended to fall within the scope of the appended claims. Further, while only certain representative devices, kits, and method steps disclosed herein are specifically described, other combinations of the devices, kits, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for ionizing a compound, comprising:
   (a) contacting a thread with a sample comprising an antigen, wherein the thread is functionalized with an antibody sufficient to capture the antigen;
   (b) forming an antibody-antigen complex and contacting the antibody-antigen complex with a reporter antibody to form a sandwich complex;
   (c) disposing the thread in a non-conductive chamber; and
   (d) applying a direct current voltage to the thread.

2. The method of claim 1, comprising disposing said non-conductive chamber in fluid communication with an analyzer.

3. The method of claim 2, wherein the analyzer is a mass spectrometer.

4. The method of claim 2, wherein the analyzer is an ion trap mass spectrometer, Orbitrap mass spectrometer, or triple quadrupole mass spectrometer.

5. The method of claim 1, wherein the applied direct current voltage is at least about 0.5 kV.

6. The method of claim 1, wherein the sample comprises a biological fluid.

7. The method of claim 1, wherein the thread comprises a cellulosic material.

8. The method of claim 7, wherein the thread is functionalized with a hydrophobic group.

9. The method of claim 8, wherein the thread is functionalized by contacting the thread with a reactive silane compound having the formula:

wherein $R^1$, $R^2$, $R^3$, and $R^4$ are independently selected from OH, $OR^a$, $NHR^a$, $N(R^a)_2$, OC(O)Ra, F, Cl, Br, or I, wherein Ra is in each case selected from $C_{1-12}$alkyl, aryl, heteroaryl, and heterocyclyl, and wherein any two or more of $R^1$, $R^2$, $R^3$, and $R^4$ can together form a ring.

10. The method of claim 1, wherein the thread has a surface energy no greater than 30 mN/m.

11. The method of claim 1, wherein the thread has a surface roughness ($S_z$) between 10-100 AU.

12. The method of claim 9, wherein the thread is functionalized by contacting the thread with a vapor comprising the reactive silane compound.

13. The method of claim 9, wherein the thread is functionalized by contacting the thread with a liquid comprising the reactive silane compound.

14. The method of claim 1, wherein the thread that is contacted with a sample is coiled around a rod, and the thread is disposed in the non-conductive chamber by sliding the rod into the chamber.

15. The method of claim 1, comprising generating a reporter compound from the sandwich complex.

16. A swab for microsampling, comprising a rod, a functionalized thread coupled to the rod, said functionalized thread coiled around at least of portion of the rod, and wherein the rod is axially slideable relative to the central axis of the coil, wherein the functionalized thread is prepared by contacting a thread with a reactive silane compound having the formula:

wherein $R^1$, $R^2$, $R^3$, and $R^4$ are independently selected from OH, $OR^a$, $NHR^a$, $N(R^a)_2$, $OC(O)R^a$, F, Cl, Br, or I, wherein Ra is in each case selected from $C_{1-12}$alkyl, aryl, heteroaryl, and heterocyclyl, and wherein any two or more of $R^1$, $R^2$, $R^3$, and $R^4$ can together form a ring.

17. An immunoassay kit, comprising:
    a thread conjugated to a capture antibody; and
    a composition comprising a reporter antibody.

18. The kit according to claim 17, wherein the thread conjugated to a capture antibody is coupled to a rod, said thread coiled around at least of portion of the rod, and wherein the rod is axially slideable relative to the central axis of the coil.

* * * * *

UNITED STATES PATENT AND TRADEMARK OFFICE
CERTIFICATE OF CORRECTION

PATENT NO. : 12,169,197 B2
APPLICATION NO. : 17/600834
DATED : December 17, 2024
INVENTOR(S) : Abraham Badu-Tawiah, Devin Swiner and Sierra Jackson Page 1 of 1

It is certified that error appears in the above-identified patent and that said Letters Patent is hereby corrected as shown below:

In the Claims

Column 15, Claim 9, Lines 37-38, reading:
from OH, OR$^a$, NHR$^a$, N (R$^a$)$_2$, OC (O) Ra, F, Cl, BR,
or I, wherein Ra is in each case selected from C$_{1-12}$al- Should read:
from OH, OR$^a$, NHR$^a$, N(R$^a$)$_2$, OC(O)R$^a$, F, Cl, BR,
or I, wherein R$^a$ is in each case selected from C$_{1-12}$al- Column 16, Claim 16, Line 31, reading:
I, wherein Ra is in each case selected from C$_{1-12}$alkyl, Should read:
I, wherein R$^a$ is in each case selected from C$_{1-12}$alkyl, Signed and Sealed this
Eleventh Day of February, 2025

Coke Morgan Stewart
*Acting Director of the United States Patent and Trademark Office*